though the Mooney method measures blood pressure from the upper arm, the tail artery pressure of rats is higher than the blood pressure measured using the Mooney method.

United States Patent [19]
Sugai et al.

[11] Patent Number: 5,703,212
[45] Date of Patent: Dec. 30, 1997

[54] PREVENTIVE FOR CIRCULATORY DISEASES

[75] Inventors: Ryuji Sugai; Umeji Murakami, both of Odawara; Yukio Yamori, Kyoto, all of Japan

[73] Assignee: Kanebo, Ltd., Tokyo, Japan

[21] Appl. No.: 727,426

[22] PCT Filed: Apr. 18, 1995

[86] PCT No.: PCT/JP95/00750

§ 371 Date: Oct. 11, 1996

§ 102(e) Date: Oct. 11, 1996

[87] PCT Pub. No.: WO95/28425

PCT Pub. Date: Oct. 26, 1995

[30] Foreign Application Priority Data

Apr. 19, 1994 [JP] Japan .................. 6-104480

[51] Int. Cl.⁶ .......... A61K 37/64; A61K 35/20; A61K 37/16

[52] U.S. Cl. .......... 530/360; 530/407; 530/343; 530/361; 514/21; 405/68.1

[58] Field of Search .......... 530/407, 343, 530/360, 361; 514/21; 405/68.1

[56] References Cited

U.S. PATENT DOCUMENTS

| | | | |
|---|---|---|---|
| 4,161,520 | 7/1979 | Osborne et al. | 424/115 |
| 4,361,564 | 11/1982 | Edwards | 424/250 |
| 5,037,957 | 8/1991 | Grubb et al. | 530/330 |

Primary Examiner—Cecilia J. Tsang
Assistant Examiner—P. Lynn Touzeau
Attorney, Agent, or Firm—Pollock, Vande Sande & Priddy

[57] ABSTRACT

A preventive for circulatory diseases which can prevent the onset of circulatory diseases, particularly cerebral stroke, without causing adverse effects such as blood-pressure fluctuation. The preventive contains as the active ingredient a low-molecular-weight peptide fraction prepared by the trypsinization of casein followed by partial purification.

20 Claims, 3 Drawing Sheets

PREVENTIVE FOR CIRCULATORY DISEASES

TECHNICAL FIELD

The present invention relates to a preventive for circulatory diseases which has the effect for the prevention of circulatory diseases, particularly cerebral stroke.

BACKGROUND OF THE INVENTION

With the recent changes in eating habits and advances in medical technology, the incidence of adults' diseases including hypertension and hyperlipemia is on the steady increase. There is a mounting interest in preventive medicine today in the face of changes in the social environment and functional substances qualified for both safety and prophylactic efficacy are gathering attention or being sought. Today the world population is leaning more and more on the higher end of the age scale, and it is the most important mission of those concerned with medical care and medical science to establish a perspective for "healthy longevity".

Model animals for diseases participated in the blood vessel which are crucial factors in human aging, namely for such diseases as circulatory diseases represented by cerebral stroke (Yamori Y. et al. Jpn. Circ. J., 38, 1095, 1974), myocardial infarction (Yamori Y. et al, Atherosclerosis, 42, 15, 1982), arteriosclerosis, multi-infarct dementia, etc., have been developed and it has been demonstrated by using such models that even in the presence of hereditary dispositions, circulatory diseases can be prevented by the proper nutrition. According to experiments using model animals, namely SHR (spontaneously hypertensive rats) (Okamoto K., et al, Jpn. Circ. J., 27, 282, 1963) and SHRSP (stroke-prone SHR), excess intake of sodium chloride encourages these diseases, while certain nutrients in food prevent them. For example, it has been shown that when soybean protein, lysine, taurine, potassium, calcium, magnesium, palmitoleic acid, etc. are administered before onset of hypertension or in an early stage after onset and onwards, they show prophylactic effects on this disease (Yamori Y., et al., New horizon in preventing cardiovascular diseases, Yamori Y. and Strasser T. eds., Elsevier, Amesterdam, pp. 1, 1989).

The factors occurring in food have also been explored and scrutinized and it has become increasingly clear that substances derived from food proteins can play a variety of physiological roles. Development of food materials having relevant activities to adults' diseases, i.e. blood cholesterol-lowering activity and antihypertensive activity (Karaki H., et al., Comp. Biochem. Physiol., 96C, 367, 1990), has been undertaken with great enthusiasm and many substances have been made available commercially as materials for performance foods (nutraceutical foods or functional foods) and foods for specified health use.

Recently, it has been reported that the ACE inhibitor, or captopril inhibits the onset of stroke in the SHRSP at a low dose just of being short of causing hypotension (Ohta Y., et al., Genetic. Hypertens., 218, 393, 1992). However, captopril has adverse side effects such as skin rush, and other substances known to be effective for circulatory diseases, particularly cerebral stroke, are objective for symptomatic treatment with undesirable adverse reactions such as blood-pressure fluctuation and so on.

Therefore, from the standpoint of preventive medicine, there has been a great standing need for substances which are highly safe, free from side effects such as blood-pressure fluctuation, prophylactively effective for the onset of circulatory diseases, particularly cerebral stroke, and inexpensive enough for daily consumption.

DISCLOSURE OF THE INVENTION

The present invention has for its object to provide a prophylactic composition for circulatory diseases which is free from adverse side effects such as blood-pressure fluctuation and effective in the prevention of circulatory diseases, inclusive of cerebral stroke in particular.

The inventors of the present invention explored a variety of foodstuffs in search for substances which would be prophylactively effective for circulatory diseases, particularly cerebral stroke, and found that a low-molecular-weight peptide fraction obtainable by hydrolyzing milk casein with trypsin and partially purifying the resulting digest is an effective prophylactic agent for circulatory diseases. The present invention has been developed on the basis of the above finding.

The present invention is now described in detail.

The casein which can be used as a substrate for the trypsin digest to be incorporated in the preventive of the present invention includes a variety of species of casein which are broadly used as food additives, and acid casein, salts of casein, rennet-casein, and so on.

The trypsin for use as a hydrolase in the present invention includes various types of trypsin which are commonly used as a reagent, for pharmaceutical applications, or as a food additive, and is preferably one which is as much free as possible from other enzymes (particularly chymotrypsin).

The trypsin hydrolysis step in the method of the present invention comprises adjusting casein, a salt of casein or the like to either neutral or alkaline, and reacting it with trypsin in aqueous solution. Preferably this reaction is carried out in the neighborhood of pH 7.5 at a protein concentration of about 10 weight % for 2 to 5 hours. The hydrolysis reaction can be terminated by an ordinary method, e.g. by heating preferably at 121° C. for 10 minutes, which conditions are conducive to complete inactivation of the enzyme and sterilization.

For the low-molecular-weight peptide fraction for use in the present invention can be separated (and purified) by the following procedure. Thus, following said termination of the hydrolysis reaction, the insoluble fraction is removed by centrifugation or filtration. The supernatant or filtrate is then fractionated by means of an ultrafiltration membrane or gel permeation chromatographic (GPC) ligand with a peptide cutoff molecular weight of about 3000 to 5000. The ultrafiltration membrane includes SEP1013 (Asahi Chemical Industry Co., Ltd.), Amikon H10 P3–20 (Grace Japan), UFP-3-E-9A (A/G Technology), etc. can be mentioned. The GPC ligand includes Sephadex G-25 (Pharmacia), Sephacryl S-100HR (Pharmacia), Bio-Gel P-6 (Bio-Rad Laboratories), Toyopearl HW-40 (Tosoh Corporation), etc. In this manner, a low-molecular-weight peptide fraction with a molecular weight of preferably not greater than 5000 and, for still better results, not greater than 3000 for use in the present invention can be obtained.

The dosage form for the preventive for circulatory diseases according to the present invention can be any form that is acceptable for pharmaceutical or food use. In particular, oral nutrition regimens, intubation nutrition regimens, beverages, tablets, ice confections, condiments, and other forms can be mentioned. The preferred proportion for use is 0.1 to 50 weight % and, for still better results, 0.5 to 10 weight % based on the whole amount of said forms.

BEST MODE OF CARRYING OUT THE INVENTION

The following example, test example, and application examples are further illustrative of the present invention. The example is an example of production of a low-molecular-weight fraction of trypsin-digested casein and the test example shows the results of prevention experiment of a circulatory disease with said low-molecular-weight fraction in SHRSPs.

Example 1

In a 50-L jar fermentor (manufactured by Mitsuwa), 3 kg of bovine milk casein (manufactured by Benie, acid casein for food use) was suspended in 30 L of water and the suspension was adjusted to pH 7.5 with 10N-KOH. With the temperature being held at 37° C., 7.5 g of trypsin (manufactured by Sigma, Type III, EC. 3. 4. 21. 4) was added and the digestion was carried out with stirring for 4 hours.

In the jar fermentor, the digest was heat-treated at high temperature and pressure (121° C., 10 minutes) and the resulting precipitate was removed by continual centrifugation at 4° C. at 10000 r.p.m. to recover a trypsin digest of casein as a supernatant.

A 5-L portion of the above trypsin digest of casein was passed through an ultrafiltration membrane to remove a high-molecular-weight peptide fraction. The ultrafiltration membrane used was SEP1013 (cutoff molecular weight= 3000) available from Asahi Chemical Industry Co., Ltd. The filtrate was freeze-dried to provide 35 g of a low-molecular-weight fraction of the trypsin digest of casein.

Test Example 1

Preventive efficacy for the circulatory disease was assayed in stroke-prone model animals (SHRSPs). Three kinds on rat diets were provided. (1) a peptide diet prepared by adding the peptide of Example 1 to a 3% NaCl ration based on Funabashi Farm's SP diet in concentration of 10 weight %, (2) an amino acid diet prepared by adding an amino acid mixture of the same composition as said peptide fraction to the 3% NaCl ration in concentration of 10 weight %, and, as a control diet, (3) the 3% NaCl ration.

Figure 1A:
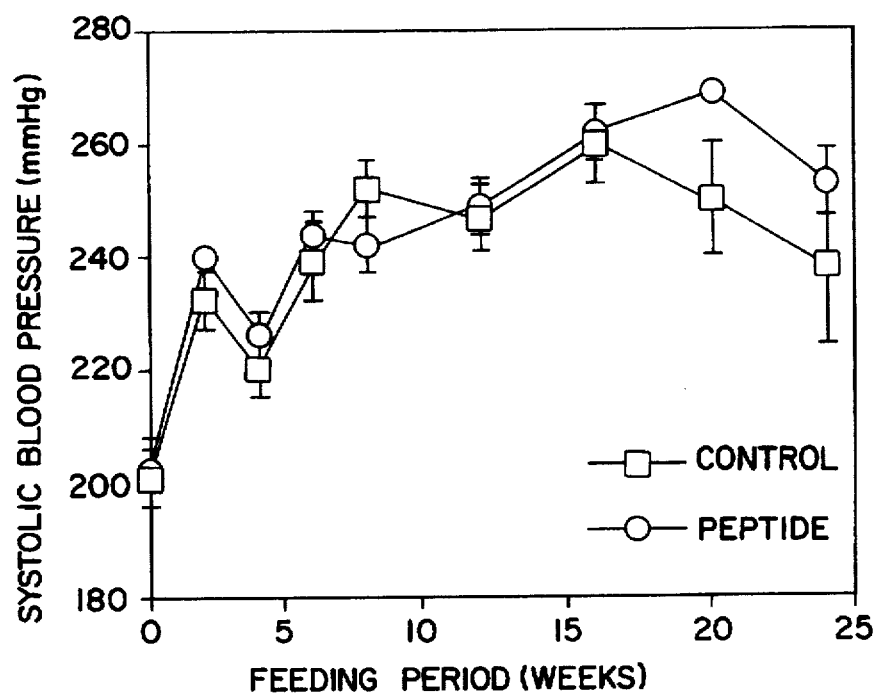
FIG. 1 is a diagram showing the time courses of (a) systolic blood pressure and (b) body weight in stroke-prone spontaneously hypertensive rats (referred to as SHRSPs) given a trypsin digest of casein. □ represents the control diet group and ○ represents the peptide diet group.
Figure 1B:
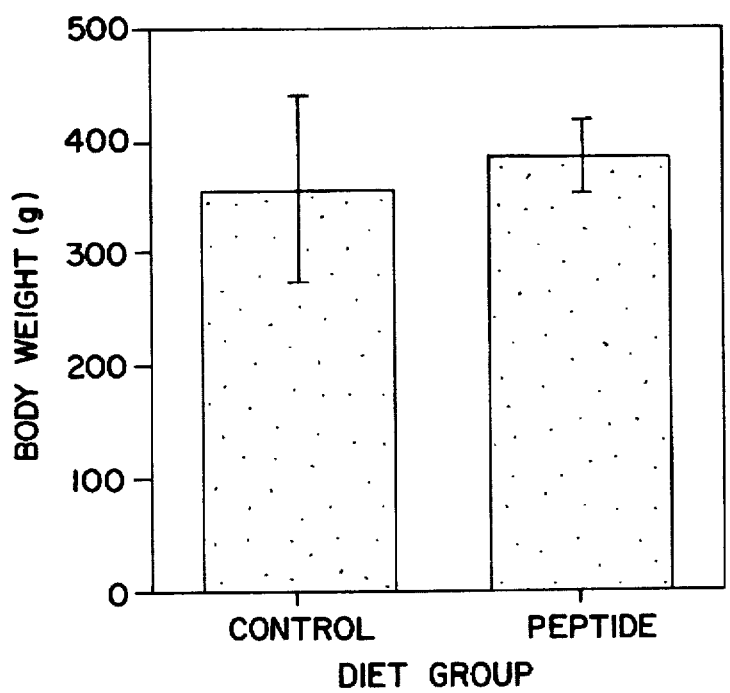

Male SHRSPs in groups of 10 were put on the peptide diet, amino acid diet, and control diet, respectively, starting day 77 after birth, and the blood pressure and body weight were determined at 2, 4, 6, 8, 12, 16, 20, and 24 weeks of feeding. All the rats surviving after 30 weeks of feeding were examined for the onset of stroke in terms of gross findings, brain weight, heart weight, and other parameters. The individuals which died in the course of observation were autopsied on occasion and similarly examined. The number of animals presenting with stroke symptoms after 30 weeks of feeding was 1 in the peptide diet group, 5 in the amino acid diet group, and 5 in the control diet group, indicating that the peptide diet prevented onset of stroke. As to blood pressure and body weight, there was no intergroup difference (FIG. 1).

Figure 2A:
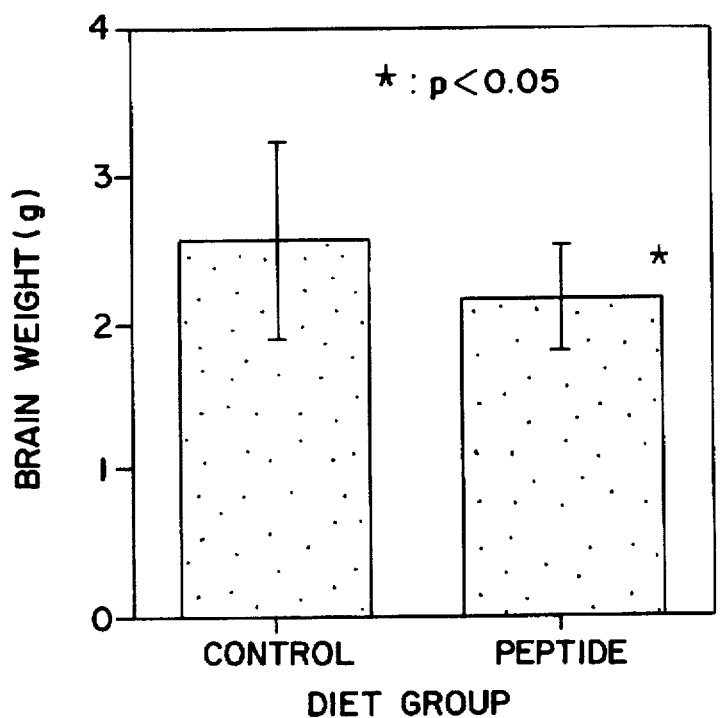
FIG. 2 is a diagrammatic representation of (a) brain weight and (b) heart weight in SHRSPs put on a diet containing trypsin digest of casein for 30 weeks, comparing the peptide diet group with the control diet group.
Figure 2B:
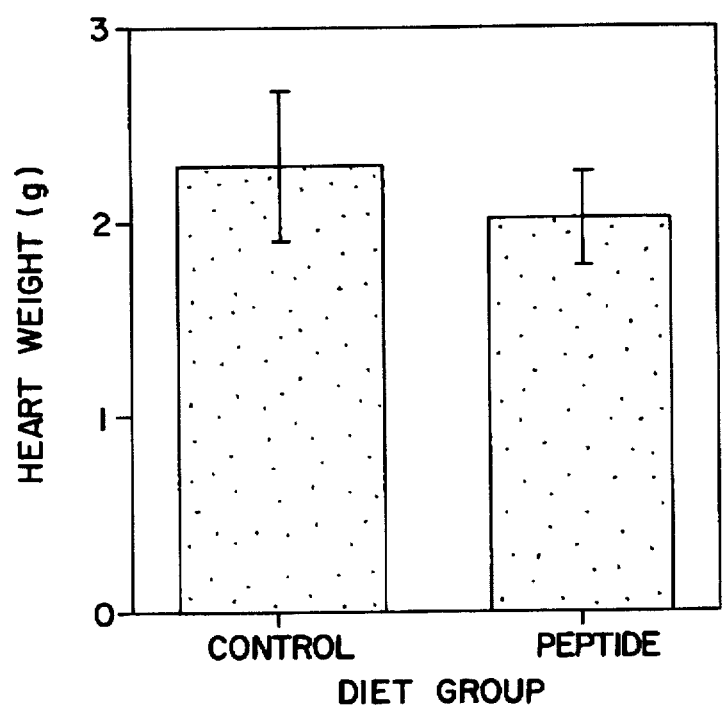

Pathological assessments (inclusive of determination of brain weight and heart weight) were carried out on dead animals at the time of death and on survivals at 30 weeks of feeding. The brain weight and heart weight data are presented in FIG. 2. In brain weight, a significant suppression of weight gain was found. In heart weight, a tendency toward suppression of weight gain was found. Thus, the peptide diet was shown to prevent brain edema and cardiac hypertrophy.

Figure 3:
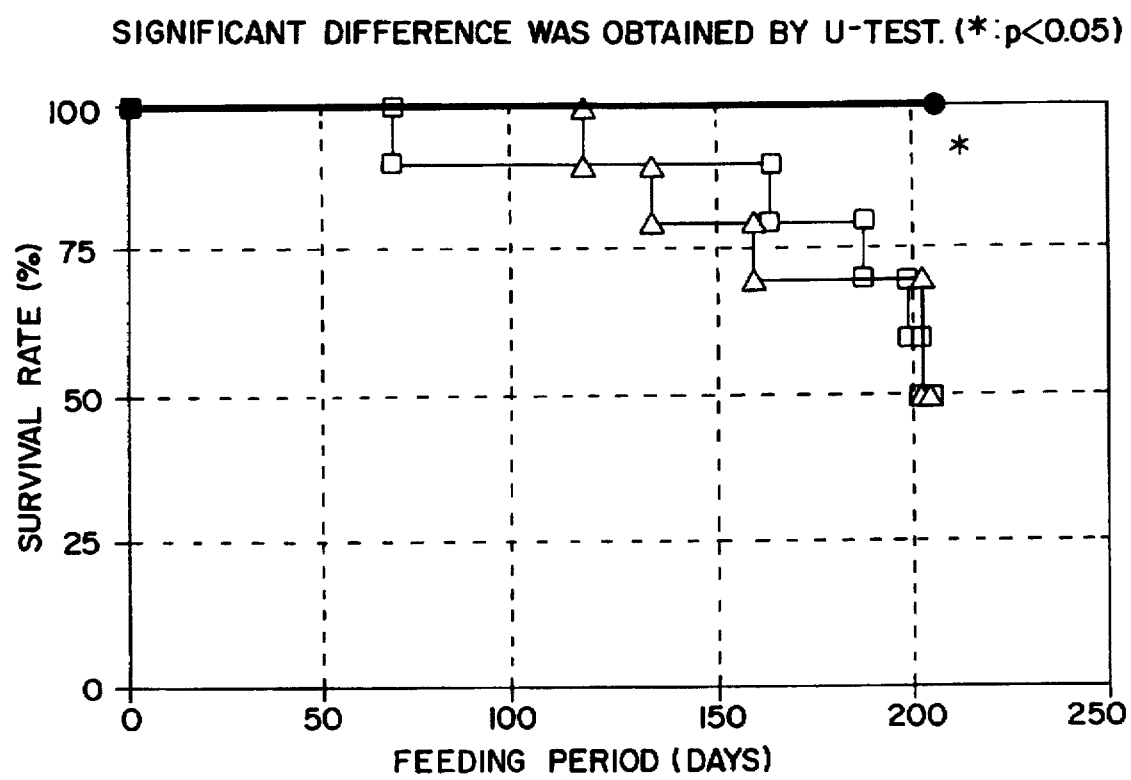
FIG. 3 is a diagram showing the time course of survival rate in SHRSPs put on a diet containing a trypsin digest of casein for 30 weeks. ● represents the peptide diet group, △ represents the amino acid diet group, and ⊔ represents the control diet group.

The time course of survival rate in each group during the feeding period was shown in FIG. 3. Whereas no death was occurred in the peptide diet group, 5 deaths each were encountered in the amino acid diet group and the control diet group. Thus, a positive longevity effect of the peptide diet was confirmed.

Application Example 1

A beverage (100 ml/bottle) was prepared according to the following formula of Table 1 in the routine manner.

TABLE 1

| | Parts by weight |
|---|---|
| Low mol. wt. peptide fraction of Example 1 | 1 |
| Beet granulated sugar | 15 |
| Citric acid | 0.4 |
| Flavoring | 0.25 |
| Water | 83.35 |

Application Example 2

Tablets (500 mg/tablet) were manufactured according to the following formula of Table 2 in the routine manner.

TABLE 2

| | Parts by weight |
|---|---|
| Low mol. wt. peptide fraction of Example 1 | 2.0 |
| Lactose | 2.2 |
| Sucrose | 0.1 |
| Carboxymethyl cellulose | 1.5 |
| Hydroxypropyl cellulose | 1.0 |
| Magnesium stearate | 0.2 |
| Starch sodium glycolate | 1.0 |

Application Example 3

An ice cream (100 g/cup) was manufactured according to the following formula of Table 3 in the routine manner.

TABLE 3

| | Parts by weight |
|---|---|
| Low mol. wt. peptide fraction of Example 1 | 1 |
| Condensed milk | 4 |
| Skim milk | 7 |
| Vegetable oil | 9 |
| Sugar | 10 |

TABLE 3-continued

|  | Parts by weight |
|---|---|
| Egg yolk | 12 |
| Stabilizer | 0.3 |
| Emulsifier | 0.4 |
| Flavoring | 0.1 |
| Water | 56.2 |

Application Example 4

A yogurt (100 g/cup) was manufactured according to the following formula of Table 4 in the routine manner.

TABLE 4

|  | Parts by weight |
|---|---|
| Low mol. wt. peptide fraction of Example 1 | 1 |
| Bovine milk | 70 |
| Whole milk | 4 |
| Skim milk | 5 |
| Granulated sugar | 7 |
| Water | 12 |
| Flavoring | 1 |

INDUSTRIAL APPLICABILITY

It is apparent that the present invention can provide a preventive for circulatory diseases which is capable of preventing onset of circulatory diseases without causing adverse effects such as blood-pressure fluctuation.

We claim:

1. A preventive for cerebral stroke which comprises a low-molecular-weight peptide fraction available on partial purification of a trypsin digest of casein as an active ingredient.

2. The preventive for cerebral stroke according to claim 1 wherein said casein is an acid casein, a salt of casein or rennet-casein.

3. The preventive for cerebral stroke according to claim 1 wherein said trypsin is a trypsin of the reagent grade, of the pharmaceutical grade, or for a food additive.

4. The preventive for cerebral stroke according to claim 1, wherein said trypsin digest is the product of a hydrolysis reaction carried out at pH 7.5 and a casein protein concentration of 10 weight % for 2 to 5 hours.

5. The preventive for cerebral stroke according to claim 1, wherein said partial purification is carried out by using an ultrafiltration membrane or gel permeation chromatographic ligand with a peptide cutoff molecular weight of not greater than 5000.

6. The preventive for cerebral stroke according to claim 1, wherein said partial purification is carried out by using an ultrafiltration membrane or gel permeation chromatographic ligand with a peptide cutoff molecular weight of not greater than 3000.

7. The preventive for cerebral stroke according to claim 1, which is provided by incorporating a low-molecular-weight peptide fraction available on partial purification of a trypsin digest of casein in a proportion of 0.1 to 50 weight % based on the whole amount.

8. The preventive for cerebral stroke according to claim 2 wherein said trypsin is a trypsin of the reagent grade, of the pharmaceutical grade, or for a food additive.

9. The preventive for cerebral stroke according to claim 2 wherein said trypsin digest is the product of a hydrolysis reaction carried out at pH 7.5 and a casein protein concentration of 10 weight % for 2 to 5 hours.

10. The preventive for cerebral stroke according to claim 3 wherein said trypsin digest is the product of a hydrolysis reaction carried out at pH 7.5 and a casein protein concentration of 10 weight % for 2 to 5 hours.

11. The preventive for cerebral stroke according to claim 2 wherein said partial purification is carried out by using an ultrafiltration membrane or gel permeation chromatographic ligand with a peptide cutoff molecular weight of not greater than 5000.

12. The preventive for cerebral stroke according to claim 3 wherein said partial purification is carried out by using an ultrafiltration membrane or gel permeation chromatographic ligand with a peptide cutoff molecular weight of not greater than 5000.

13. The preventive for cerebral stroke according to claim 4 3 wherein said partial purification is carried out by using an ultrafiltration membrane or gel permeation chromatographic ligand with a peptide cutoff molecular weight of not greater than 5000.

14. The preventive for cerebral stroke according to claim 2 wherein said partial purification is carried out by using an ultrafiltration membrane or gel permeation chromatographic ligand with a peptide cutoff molecular weight of not greater than 3000.

15. The preventive for cerebral stroke according to claim 3 wherein said partial purification is carried out by using an ultrafiltration membrane or gel permeation chromatographic ligand with a peptide cutoff molecular weight of not greater than 3000.

16. The preventive for cerebral stroke according to claim 4 wherein said partial purification is carried out by using an ultrafiltration membrane or gel permeation chromatographic ligand with a peptide cutoff molecular weight of not greater than 3000.

17. The preventive for cerebral stroke according to claim 5 wherein said partial purification is carried out by using an ultrafiltration membrane or gel permeation chromatographic ligand with a peptide cutoff molecular weight of not greater than 3000.

18. The preventive for cerebral stroke according to claim 2 which is provided by incorporating a low-molecular-weight peptide fraction available on partial purification of a trypsin digest of casein in a proportion of 0.1 to 50 weight % based on the whole amount.

19. The preventive for cerebral stroke according to claim 3 which is provided by incorporating a low-molecular-weight peptide fraction available on partial purification of a trypsin digest of casein in a proportion of 0.1 to 50 weight % based on the whole amount.

20. The preventive for cerebral stroke according to claim 4 which is provided by incorporating a low-molecular-weight peptide fraction available on partial purification of a trypsin digest of casein in a proportion of 0.1 to 50 weight % based on the whole amount.

* * * * *